United States Patent
Biermann

(10) Patent No.: US 7,386,975 B2
(45) Date of Patent: Jun. 17, 2008

(54) METHOD FOR DETERMINING THE EFFECTS OF FANCY YARN

(75) Inventor: Iris Biermann, Mönchengladbach (DE)

(73) Assignee: Oerlikon Textile GmbH & Co. KG, Monchengladbach (DE)

( * ) Notice: Subject to any disclaimer, the term of this patent is extended or adjusted under 35 U.S.C. 154(b) by 68 days.

(21) Appl. No.: 10/575,566

(22) PCT Filed: Sep. 16, 2004

(86) PCT No.: PCT/EP2004/010368

§ 371 (c)(1),
(2), (4) Date: Apr. 11, 2006

(87) PCT Pub. No.: WO2005/037699

PCT Pub. Date: Apr. 28, 2005

(65) Prior Publication Data
US 2007/0022728 A1    Feb. 1, 2007

(30) Foreign Application Priority Data
Oct. 16, 2003  (DE) ............... 103 48 742

(51) Int. Cl.
*D01H 13/26*  (2006.01)
(52) U.S. Cl. .................................. 57/265
(58) Field of Classification Search ............... 57/265
See application file for complete search history.

(56) References Cited

U.S. PATENT DOCUMENTS

| 3,303,698 | A | | 2/1967 | Loepfe ..................... 73/160 |
| 3,887,814 | A | * | 6/1975 | Faulhaber ............... 250/559.39 |
| 3,986,037 | A | * | 10/1976 | Faulhaber ............... 250/559.2 |
| 4,168,604 | A | * | 9/1979 | Mannhart ..................... 57/264 |
| 4,891,974 | A | * | 1/1990 | Wassenhoven ............... 73/160 |
| 4,906,519 | A | * | 3/1990 | Stanko et al. ............... 442/400 |
| 4,924,406 | A | * | 5/1990 | Bergamini et al. .......... 700/143 |
| 5,119,308 | A | * | 6/1992 | Samoto ..................... 700/139 |
| 5,748,481 | A | * | 5/1998 | Nakade ..................... 700/143 |
| 6,130,746 | A | * | 10/2000 | Nevel et al. ............. 356/238.2 |
| 6,244,030 | B1 | * | 6/2001 | Arb et al. ..................... 57/264 |
| 6,741,726 | B1 | * | 5/2004 | Nevel et al. ................. 382/111 |

FOREIGN PATENT DOCUMENTS

DE    100 26 389 A1    3/2001

OTHER PUBLICATIONS

Patent Abstracts of Japan—JP 02-221427, Sep. 4, 1990.
Patent Abstracts of Japan—JP 06-128821, May 10, 1994.

* cited by examiner

*Primary Examiner*—Shaun R. Hurley
(74) *Attorney, Agent, or Firm*—Kennedy Covington Lobdell & Hickman, LLP

(57) ABSTRACT

A method for determining the effects of a fancy yarn by measuring the yarn diameter. The yarn sections between the effect areas are referred to as webs. The effect area is determined in that the beginning of the effect is defined by meeting a first criterion and the end of the effect is defined by meeting a second criterion. A specifiable number of the largest diameters is determined between the beginning and end of the effect, an average is formed from the diameters determined, which is specified as the diameter of the effect, and the effect length is determined from the beginning and end of the effect.

12 Claims, 3 Drawing Sheets

METHOD FOR DETERMINING THE EFFECTS OF FANCY YARN

CROSS-REFERENCES TO RELATED APPLICATIONS

This application claims the benefit of German patent application 10348742.5, filed Oct. 16, 2003, herein incorporated by reference.

BACKGROUND OF THE INVENTION

The invention relates to a method for determining the effects of a fancy yarn, sometimes also referred to as a novelty yarn or an effect yarn, by measuring the yarn diameter, wherein the yarn sections between the effect areas are referred to as webs.

When producing yarn, a uniformity of the yarn, which is as high as possible, is generally aimed for within narrow tolerances. On the other hand, the non-uniformity of the yarn is characteristic of fancy yarns. A yarn, in which thick locations with predetermined larger diameters and with predetermined lengths, the so-called effects, are present, are referred to as fancy yarns, also commonly referred to as novelty or effect yarns. The yarn sections located therebetween with a smaller diameter are referred to as webs.

It is known to carry out a diameter average value determination at the beginning of measuring at a spinning station, over the first yarn meter. This so-called reference diameter is the reference diameter for further evaluations. In the case of a fancy yarn, a reference diameter determined in this manner would be indicated to be thicker owing to the presence of effects, in other words thick locations, than the thickness of the web actually is. The recognition of the formation of effects is only possible on this basis of a simple averaging to an inadequate degree.

SUMMARY OF THE INVENTION

The object of the invention is to improve the determination of effects of a fancy yarn.

This object is achieved by a method for determining the effects of a fancy yarn by measuring the yarn diameter. The yarn sections between the effect areas are referred to as webs. According to the invention, the effect area is determined in that the beginning of the effect is defined by meeting a first criterion and the end of the effect is defined by meeting a second criterion. A specifiable number of the largest diameters is determined between the beginning and end of the effect, an average is formed from the diameters determined, which is specified as the diameter of the effect, and the effect length is determined from the beginning and end of the effect.

Additional advantageous configurations and aspects of the invention are described below.

The method according to the invention makes it possible to recognize the effects better and to determine the effect diameter, also referred to as the effect thickness, and the effect length more correctly.

To determine the web diameter $D_{ST}$, an arithmetic average of the yarn diameter is initially formed from a predetermined length of yarn as the reference diameter. The reference diameter is subtracted from the individual values of the yarn diameter, and the web diameter $D_{ST}$ is then formed as the arithmetic average from all negative values, which were measured adjacent to other negative values. The web diameter, also called the web thickness, as thusly determined is largely uninfluenced by the effects and therefore substantially more accurate than is possible with the known simple reference value formation in yarn measurements. This increased accuracy also has a positive effect on the accuracy of the effect determination.

The diameter $D_E$ of the effect may be formed as an average from the four largest diameters between the beginning and end of the effect. It can be avoided that only a very brief exceeding or falling below of the limit diameter leads to a falsification of the effect length.

A variation value is advantageously determined, which provides the variation of the diameter over the effect length. For this purpose, the diameter is continuously measured within the effect length. The variation value can be provided as the average quadratic non-uniformity that provides information about the uniformity of the effect course. Conclusions about the quality of the subsequent end product, for example a fabric, can be drawn from the variation value. A high uniformity allows a clean image of the effects in the fabric to be expected, a lower uniformity, on the other hand, a blurred image. Determination of the average quadratic non-uniformity corresponds to the known detection of the so-called CV value in the case of smooth yarn.

The method according to the invention allows detection of the effect length and effect thickness with values, which very closely approach the real configuration and therefore allow reliable information about the quality of the fancy yarn and the end product.

BRIEF DESCRIPTION OF THE DRAWINGS

Further details of the invention can be found in the figures. In the figures.

DESCRIPTION OF THE PREFERRED EMBODIMENTS

Figure 1:
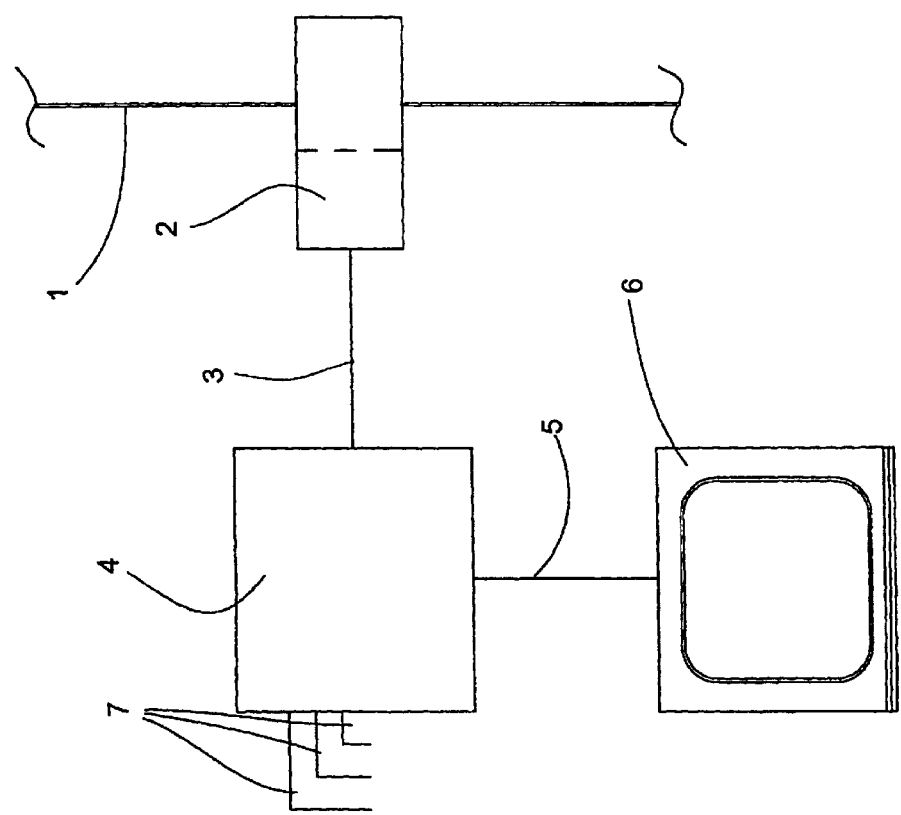
FIG. 1 shows a device for carrying out the method according to the invention.

FIG. 1 shows a section of a fancy yarn 1, which runs through a sensor 2, which is provided to measure the yarn diameter D. The sensor 2 is an optical sensor, as is known in principle, and which will not therefore be described in detail here. The sensor 2 is connected via a line 3 to the evaluation unit 4. The evaluation unit 4 determines the desired effect data from the measured values of the yarn diameter D transmitted by the sensor 2. The evaluation unit 4 transmits the effect data via the line 5 to an output mechanism comprising a monitor 6. The effect data can be shown in the desired form on the monitor 6.

The evaluation unit 4 is connected via the lines 7 to further evaluation units or computers, not shown.

Figure 2:
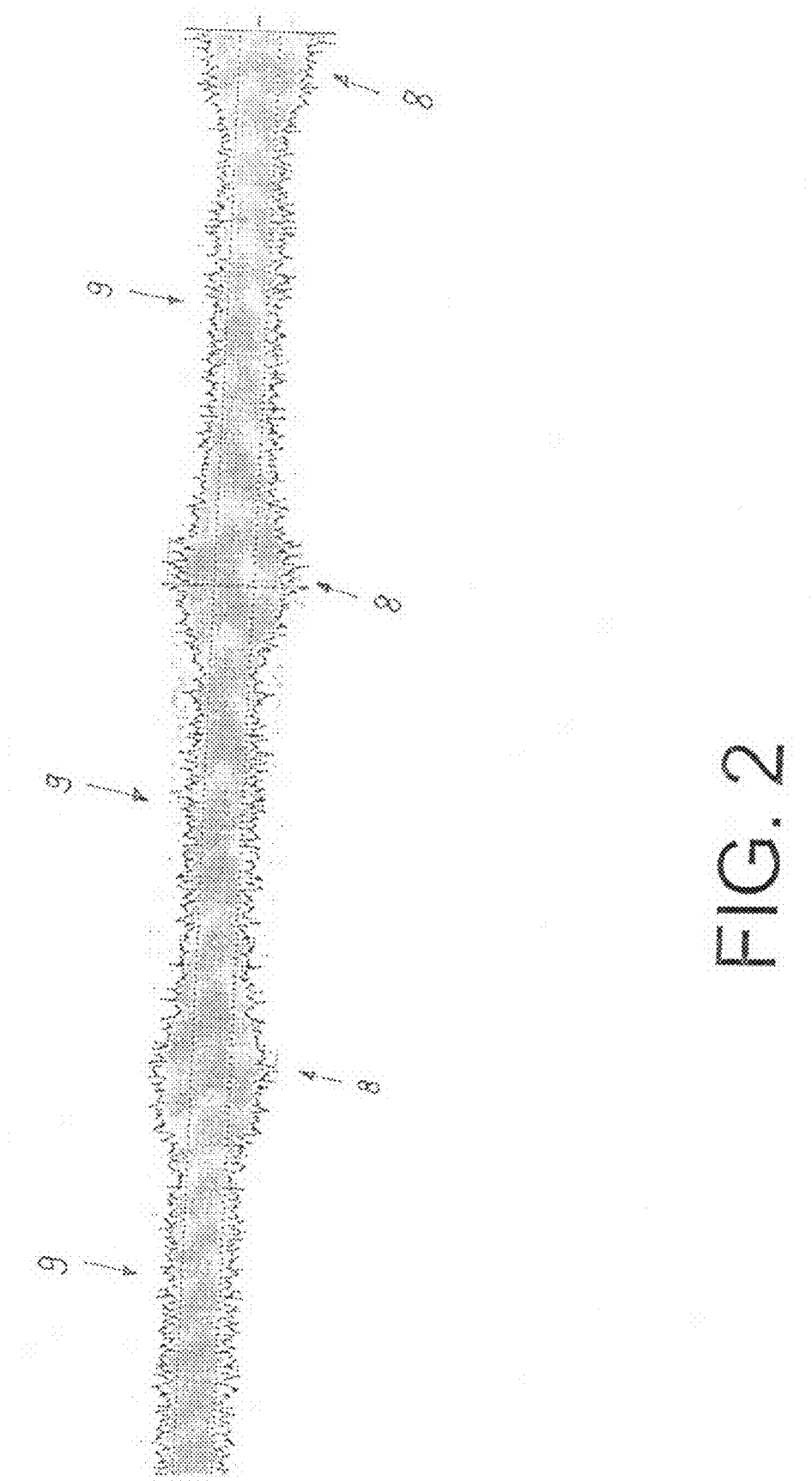
FIG. 2 shows a fancy yarn, which is shown by arranging measured values of the yarn diameter side by side.

FIG. 2 shows the view of the fancy yarn 1, as measured values arranged side by side. Effects 8 and webs 9 can be seen but the beginning and end of the effects 8 and the effect thickness or the effect diameter $D_E$ and the web thickness or the web diameter $D_{ST}$ cannot be recognized clearly and therefore not adequately.

Figure 3:
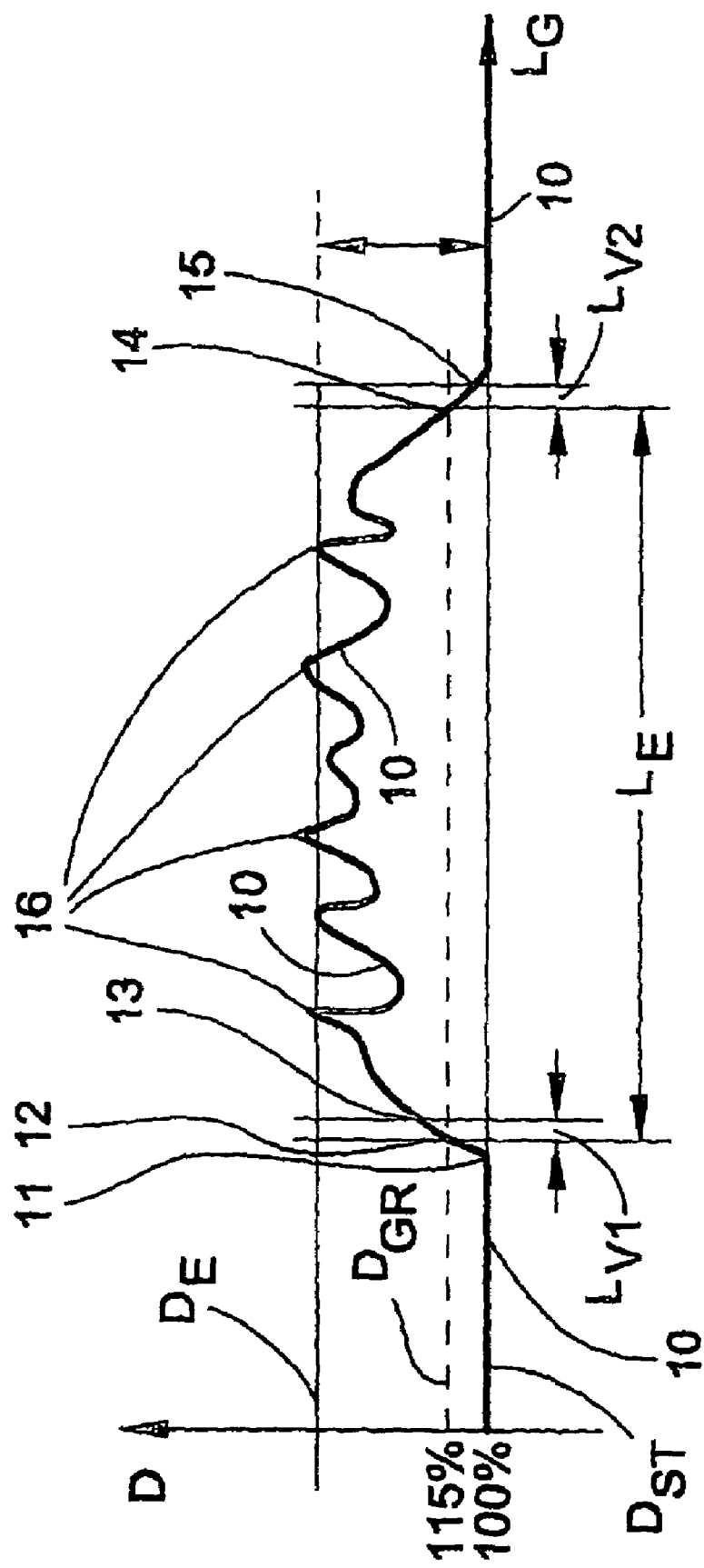
FIG. 3 shows a schematic diagram of a yarn effect.

The evaluation unit 4 registers the yarn diameter D after 2 mm yarn length, in each case. A cycle represents a measuring length of 2 mm yarn. In the view of FIG. 3, the yarn diameter D is shown in a percentage over the yarn length $L_G$ as a curve 10. The curve 10 represents the web diameter $D_{ST}$ in the view of FIG. 3 beginning from the left up to the point 11. From the point 11 the curve 10 rises and, at point 12, passes the value of the limit diameter $D_{GR}$. At point 13, the predetermined yarn length $L_{V1}$ has been covered since reaching the point 12. After a diameter increase of 15% is registered at point 12, and the exceeding of the limit diameter $D_{GR}$ continues over the predetermined length $L_{V1}$, for example for six cycles or 12 mm, the point 12 is defined as the beginning of the effect. The curve 10 falls below the limit diameter $D_{GR}$ at the point 14. The falling below last until point 15 and therefore over the predetermined yarn length $L_{V2}$. Therefore, the point 14 is defined as the end of the effect. The effect length $L_E$ is determined from the beginning and end of the effect between point 12 and point 14. An arithmetic average is formed from the four largest diameters 16 within the effect. The provision of the effect diameter is therefore largely independent of the natural diameter variations in the effect area. This arithmetic average is defined as the effect diameter $D_E$.

A variation value, which makes a statement about the quality of the effects 8 possible, is determined on the basis of the variations of the yarn diameter D, which can be recognized in FIGS. 2 and 3, in the area of the effect length of the effects 8. The variation value provides the average quadratic non-uniformity and is a measure of the uniformity of the effect course. The higher the uniformity of the effect course, the better the quality of the fancy yarn 1 and the end product produced therefrom, for example a fabric. The variation value is the relative dispersion of the individual values around the average of the yarn diameter D within the effect length.

Further configurations of the method within the scope of the invention are possible. The method according to the invention is not limited to the embodiment shown.

The invention claimed is:

1. Method for determining the effects of a fancy yarn by measuring the yarn diameter, wherein the yarn sections between the effect areas are referred to as webs, characterized in that the effect area is determined in that the beginning of the effect is defined by meeting a first criterion and the end of the effect is defined by meeting a second criterion, in that a specifiable number of the largest diameters is determined between the beginning and end of the effect, in that an average is formed from the diameters determined, which is specified as the diameter of the effect, and in that the effect length is determined from the beginning and end of the effect.

2. Method according to claim 1, characterized in that the web diameter $D_{ST}$ is determined, in order to determine the relative effect thickness.

3. Method according to claim 1, characterized in that to determine the web diameter $D_{ST}$, an arithmetic average of the yarn diameter is initially formed from a predetermined length of yarn as the reference diameter, in that the reference diameter is subtracted from the individual values of the yarn diameter, and in that the web diameter $D_{ST}$ is then formed as the arithmetic average from all negative values, which were measured adjacent to other negative values.

4. Method according to claim 1, characterized in that the diameter $D_E$ of the effect is formed as an average from the four largest diameters between the beginning and end of the effect.

5. Method according to claim 1, characterized in that the exceeding of a limit diameter $D_{GR}$ applies as the first criterion, which diameter is greater by a defined amount than the web diameter $D_{ST}$ and in that the exceeding lasts over a predetermined yarn length $L_{V1}$ and in that the falling below of the limit diameter $D_{GR}$ applies as the second criterion and the falling below lasts over a predetermined yarn length $L_{V2}$.

6. Method according to claim 5, characterized in that the limit diameter $D_{GR}$ is 15% greater than the web diameter $D_{ST}$.

7. Method according to claim 5, characterized in that the predetermined yarn length is then taken to be reached when the criterion is met over six consecutive measured values.

8. Method according to claim 1, characterized in that a measured value is detected every two millimeters when measuring the yarn diameter.

9. Method according to claim 1, characterized in that the variation in the diameter is determined on the effect length.

10. Method for determining the effects of a fancy yarn by measuring the yarn diameter, wherein the yarn sections between the effect areas are referred to as webs, characterized in that the effect area is determined in that the beginning of the effect is defined by meeting a first criterion and the end of the effect is defined by meeting a second criterion, in that a specifiable number of the largest diameters is determined between the beginning and end of the effect, in that an average is formed from the diameters determined, which is specified as the diameter of the effect, and in that the effect length is determined from the beginning and end of the effect, the method being characterized in that the exceeding of a limit diameter $D_{GR}$ applies as the first criterion, which diameter is greater by a defined amount than the web diameter $D_{ST}$ and in that the exceeding lasts over a predetermined yarn length $L_{V1}$ and in that the falling below of the limit diameter $D_{GR}$ applies as the second criterion and the falling below lasts over a predetermined yarn length $L_{V2}$.

11. Method according to claim 10, characterized in that the limit diameter $D_{GR}$ is 15% greater than the web diameter $D_{ST}$.

12. Method according to claim 10, characterized in that the predetermined yarn length is then taken to be reached when the criterion is met over six consecutive measured values.

* * * * *